US009655604B2

(12) United States Patent
Tegels et al.

(10) Patent No.: US 9,655,604 B2
(45) Date of Patent: May 23, 2017

(54) BLOCKING SLEEVE FOR BIOADHESIVE DELIVERY DEVICE AND METHODS

(71) Applicant: St. Jude Medical Puerto Rico LLC, Caguas, PR (US)

(72) Inventors: Zachary J. Tegels, Minneapolis, MN (US); Robert M. Vidlund, Forest Lake, MN (US); Martha Escobar, Jordan, MN (US); Edward E. Parsonage, St. Paul, MN (US); Russell D. Terwey, St. Michael, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 549 days.

(21) Appl. No.: 13/778,798

(22) Filed: Feb. 27, 2013

(65) Prior Publication Data
US 2014/0135825 A1  May 15, 2014

Related U.S. Application Data

(60) Provisional application No. 61/726,305, filed on Nov. 14, 2012.

(51) Int. Cl.
*A61B 17/00* (2006.01)

(52) U.S. Cl.
CPC .... *A61B 17/0057* (2013.01); *A61B 17/00491* (2013.01); *A61B 2017/0065* (2013.01);
(Continued)

(58) Field of Classification Search
CPC  A61B 2017/00672; A61B 2017/00601; A61B 2017/0065; A61B 2017/00654; A61B 17/0057
See application file for complete search history.

(56) References Cited

U.S. PATENT DOCUMENTS 6,045,569 A    4/2000 Kensey et al.
6,090,130 A    7/2000 Nash et al.
(Continued)

FOREIGN PATENT DOCUMENTS

WO    WO2011/025529    *  3/2011  ............. A61B 17/00
WO    2012148745 A1    11/2012

OTHER PUBLICATIONS

U.S. Appl. No. 13/770,586, filed Feb. 19, 2013.
(Continued)

*Primary Examiner* — Thomas McEvoy
(74) *Attorney, Agent, or Firm* — Holland & Hart

(57) ABSTRACT

A closure assembly includes an insertion sheath insertable into a tissue puncture and a tissue puncture closure device insertable through the insertion sheath and into the tissue puncture. The tissue puncture closure device includes a dual lumen delivery tube, a first sealing sleeve, and a second sealing sleeve. The dual lumen delivery tube has a first lumen configured to deliver a volume of sealing material to the tissue puncture, and a second lumen sized for insertion of a balloon location device. The first sealing sleeve is positioned between an outer surface of the dual lumen delivery tube and an inner surface of the insertion sheath to limit backflow of the sealing material into the insertion sheath. The second sealing sleeve is positioned between an outer surface of the balloon location device and an inner surface of the second lumen to limit backflow of the sealing material into the second lumen.

15 Claims, 8 Drawing Sheets

(52) U.S. Cl.
CPC ............... *A61B 2017/00557* (2013.01); *A61B 2017/00601* (2013.01); *A61B 2017/00654* (2013.01); *A61B 2017/00672* (2013.01)

(56) References Cited

U.S. PATENT DOCUMENTS

| | | | |
|---|---|---|---|
| 6,733,515 B1* | 5/2004 | Edwards et al. | 606/214 |
| 8,333,787 B2 | 12/2012 | Pipenhagen et al. | |
| 8,506,592 B2 | 8/2013 | Killion et al. | |
| 2004/0249342 A1* | 12/2004 | Khosravi et al. | 604/96.01 |
| 2007/0021772 A1* | 1/2007 | von Oepen et al. | 606/194 |
| 2010/0211000 A1* | 8/2010 | Killion et al. | 604/57 |
| 2011/0166595 A1 | 7/2011 | Vidlund et al. | |
| 2011/0282383 A1 | 11/2011 | Vidlund et al. | |
| 2012/0245517 A1 | 9/2012 | Tegels | |
| 2013/0006299 A1 | 1/2013 | Pipenhagen et al. | |
| 2013/0190808 A1 | 7/2013 | Tegels et al. | |
| 2013/0190812 A1 | 7/2013 | Vidlund | |
| 2013/0190813 A1 | 7/2013 | Tegels et al. | |

OTHER PUBLICATIONS

U.S. Appl. No. 13/770,714, filed Feb. 19, 2013.
U.S. Appl. No. 13/772.834, filed Feb. 21, 2013.
U.S. Appl. No. 13/773,062, filed Feb. 21, 2013.
U.S. Appl. No. 13/773,206, filed Feb. 21, 2013.
PCT International Search Report for International Application No. PCT/US2013/027849, mailed Sep. 12, 2013, (6 pp.).

* cited by examiner

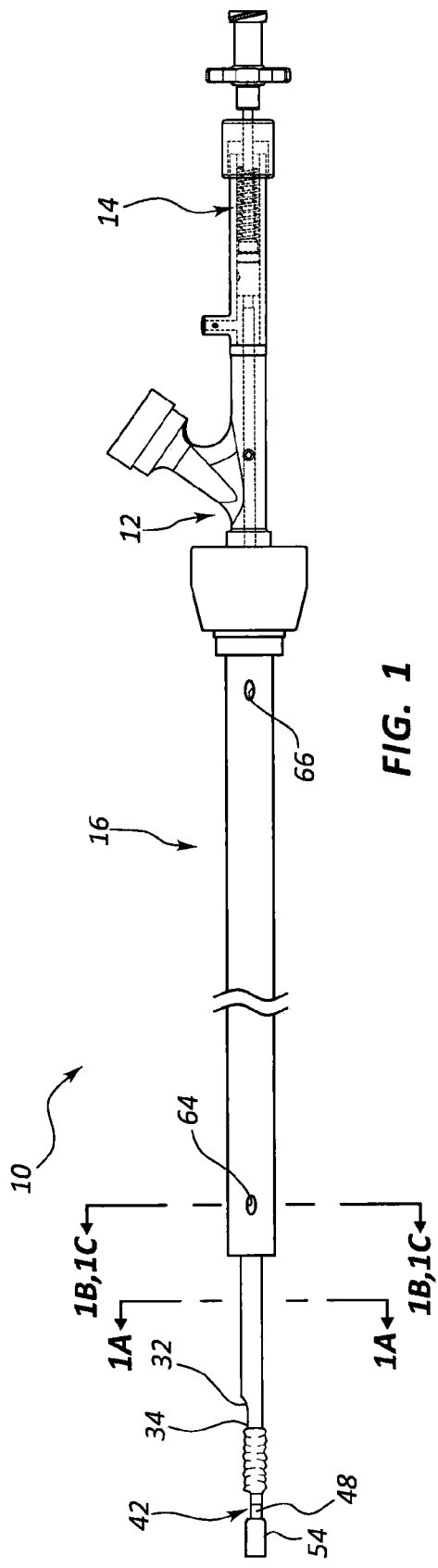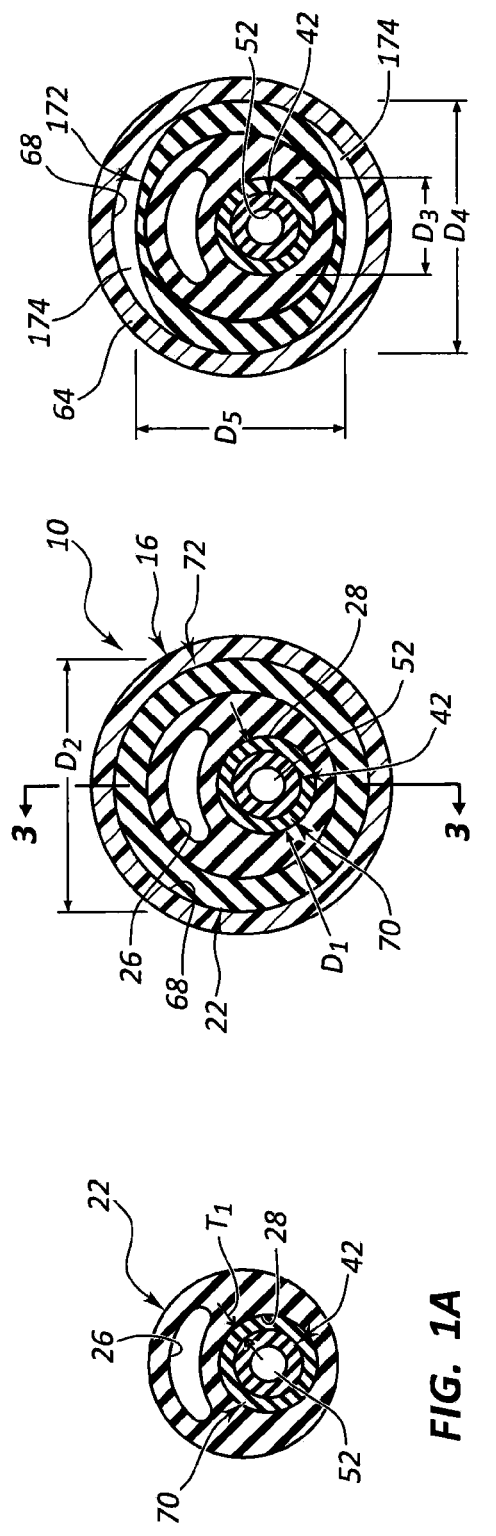

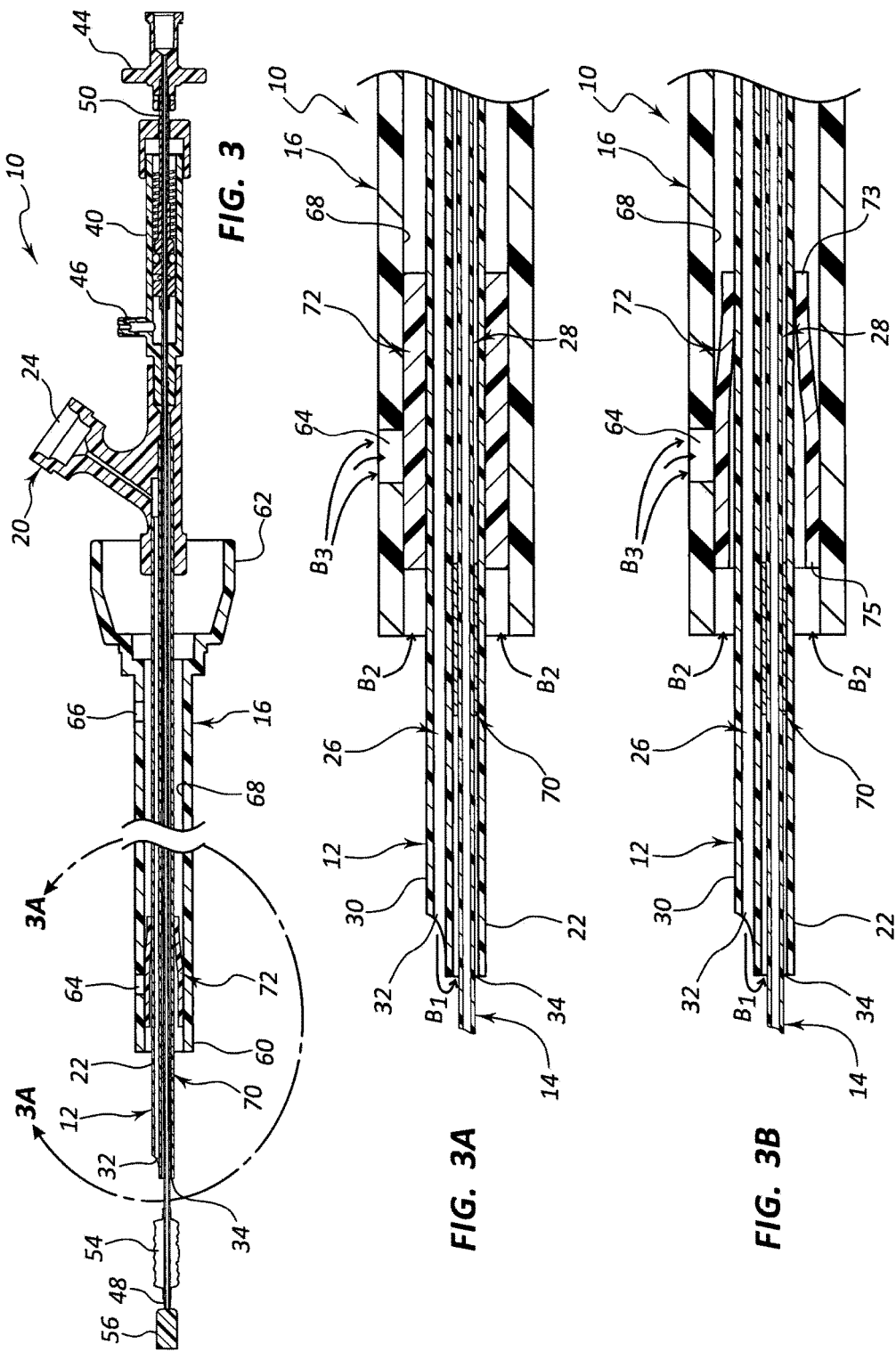

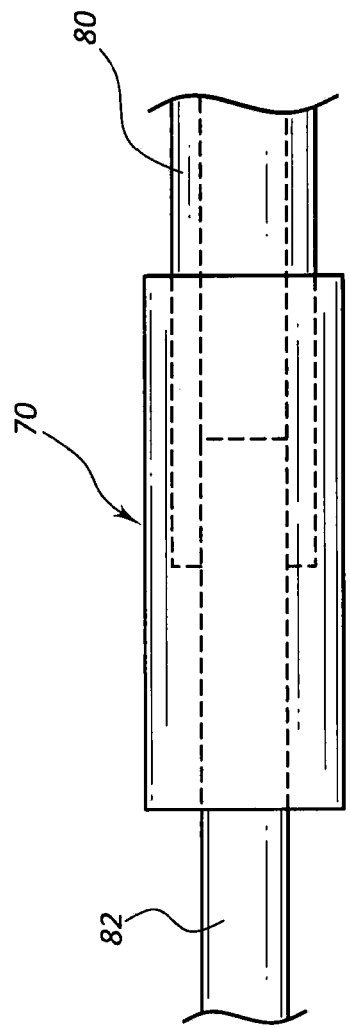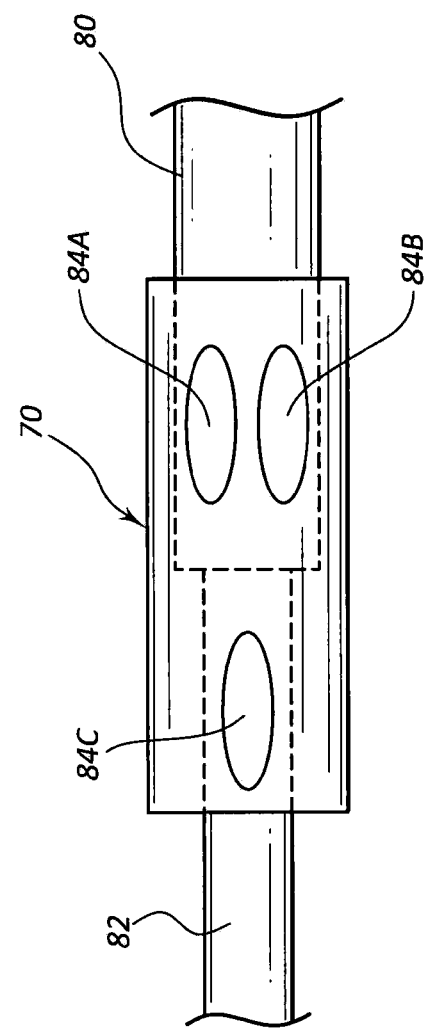

BLOCKING SLEEVE FOR BIOADHESIVE DELIVERY DEVICE AND METHODS

RELATED APPLICATION

This claims the benefit of U.S. Provisional Application No. 61/726,305, filed 14 Nov. 2012, which is hereby incorporated by reference herein in its entirety.

TECHNICAL FIELD

The present disclosure relates generally to methods and systems for sealing tissue punctures, and more particularly, to methods and systems for controlling backflow of bioadhesive sealant used to seal the tissue puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties by this reference.

While there are a variety of prior art devices and techniques for closing such punctures, one method includes temporarily sealing the tissue puncture intravascularly using an inflation balloon. A sealing material may be delivered to an outer surface of the tissue to seal the tissue puncture while the temporary seal from the balloon is maintained. Challenges exist in controlling flow of the sealing material relative to the device being used to deliver the sealing material to the tissue puncture.

SUMMARY

One aspect of the present disclosure relates to a closure assembly that includes an insertion sheath and a tissue puncture closure device. The insertion sheath is insertable into a tissue puncture. The tissue puncture closure device is insertable through the insertion sheath and into the tissue puncture. The tissue puncture closure device includes a dual lumen delivery tube and at least one of a first sealing sleeve and a second sealing sleeve. The dual lumen delivery tube has a first lumen configured to deliver a volume of sealing material to the tissue puncture, and a second lumen sized for insertion of a balloon location device. The first sealing sleeve is positioned between an outer surface of the dual lumen delivery tube and an inner surface of the insertion sheath to limit backflow of the sealing material into the insertion sheath. The second sealing sleeve is positioned between an outer surface of the balloon location device and an inner surface of the second lumen to limit backflow of the sealing material into the second lumen.

The first sleeve may be connected to the outer surface of the dual lumen delivery tube. The second sleeve may be connected to the outer surface of the balloon location device. The first and second sleeves may include a continuous loop of compliant material. The first and second sleeves may each have a tubular construction with a circular cross section. The first sleeve may have an oval shaped outer perimeter and a circular shaped inner perimeter. The first sleeve may be connected to the dual lumen delivery tube with an adhesive. The first sleeve may be connected to the dual lumen delivery tube with one of a heat weld and a laser weld.

The tissue puncture closure device may also include an inflation balloon positioned at a distal end of the balloon location device, and the second sheath is positioned proximal of the inflation balloon. The insertion sheath may include at least one location port defined in a sidewall thereof, wherein the first sleeve overlaps the at least one location port.

Another aspect of the present disclosure relates to a tissue puncture closure device that includes a balloon location device, a delivery tube, and first and second sealing sleeves. The balloon location device has an inflation balloon positioned at a distal end portion thereof. The delivery tube has a first lumen configured to deliver a volume of sealant and a second lumen sized to receive the balloon location device. A distal end of the delivery tube is insertable through an insertion sheath to a tissue puncture. The first sealing sleeve is positioned between an outer surface of the delivery tube and an inner surface of the insertion sheath to limit backflow of the sealant into the insertion sheath. The second sealing sleeve is positioned between an outer surface of the balloon location device and an inner surface of the second lumen to limit backflow of the sealant into the second lumen.

The first and second sealing sleeves may be continuous tubular shaped structures. The first and second sealing sleeves may include compliant material. At least one of the first and second sleeves may include a circular inner cross-sectional shape and a non-circular outer cross-sectional shape. The first sleeve may contact the inner surface of the insertion sheath at spaced apart locations around a circumference of the inner surface. The first sleeve may be connected to the delivery tube and the second sleeve may be connected to the balloon location device. The first sealing sleeve may be connected to the inner surface of the insertion sheath.

Another aspect of the present disclosure relates to a method of delivering a bioadhesive sealant for use in sealing a tissue puncture. The method includes providing a tissue puncture closure device and an insertion sheath, the tissue puncture closure device comprising a balloon location device and a delivery tube having first and second lumens. The method also includes inserting the insertion sheath into the tissue puncture, inserting the tissue puncture closure device into the insertion sheath until a distal end of the delivery tube extends distal of a distal end of the insertion sheath and a distal end of the balloon location device extends distal of the distal end of the delivery tube, and forming a first seal between an outer surface of the delivery tube and an inner surface of the insertion sheath.

The method may include forming a second seal between an outer surface of the balloon location device and an inner surface of a lumen of the delivery tube. The tissue puncture closure device may include a first sealing sleeve positioned on the outer surface of the delivery tube to form the first seal. The tissue puncture closure device may include a second sealing sleeve positioned on the outer surface of the balloon location device to form the second seal.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1 is a side view of an example vascular closure system in accordance with the present disclosure.

FIG. 1A is a cross-sectional view of the vascular closure system of FIG. 1 taken along cross-section indicators 1A-1A.

FIGS. 1B and 1C are cross-sectional views of the vascular closure system of FIG. 1 taken along cross-section indicators 1B,1C-1B,1C.

FIG. 3 is a cross-sectional view of the vascular closure system of FIG. 1B taken along cross-section indicators 3-3.

FIG. 3A is a close-up view of a distal end portion of the vascular closure system of FIG. 3.

FIG. 3B is a close-up view of the vascular closure system of FIG. 3 comprising an alternative sealant sleeve configuration.

FIG. 4A shows an example sealant sleeve in accordance with the present disclosure.

FIG. 4B shows another example sealant sleeve in accordance with the present disclosure.

Throughout the drawings, identical reference numbers designate similar, but not necessarily identical, elements.

DETAILED DESCRIPTION

Figure 2:
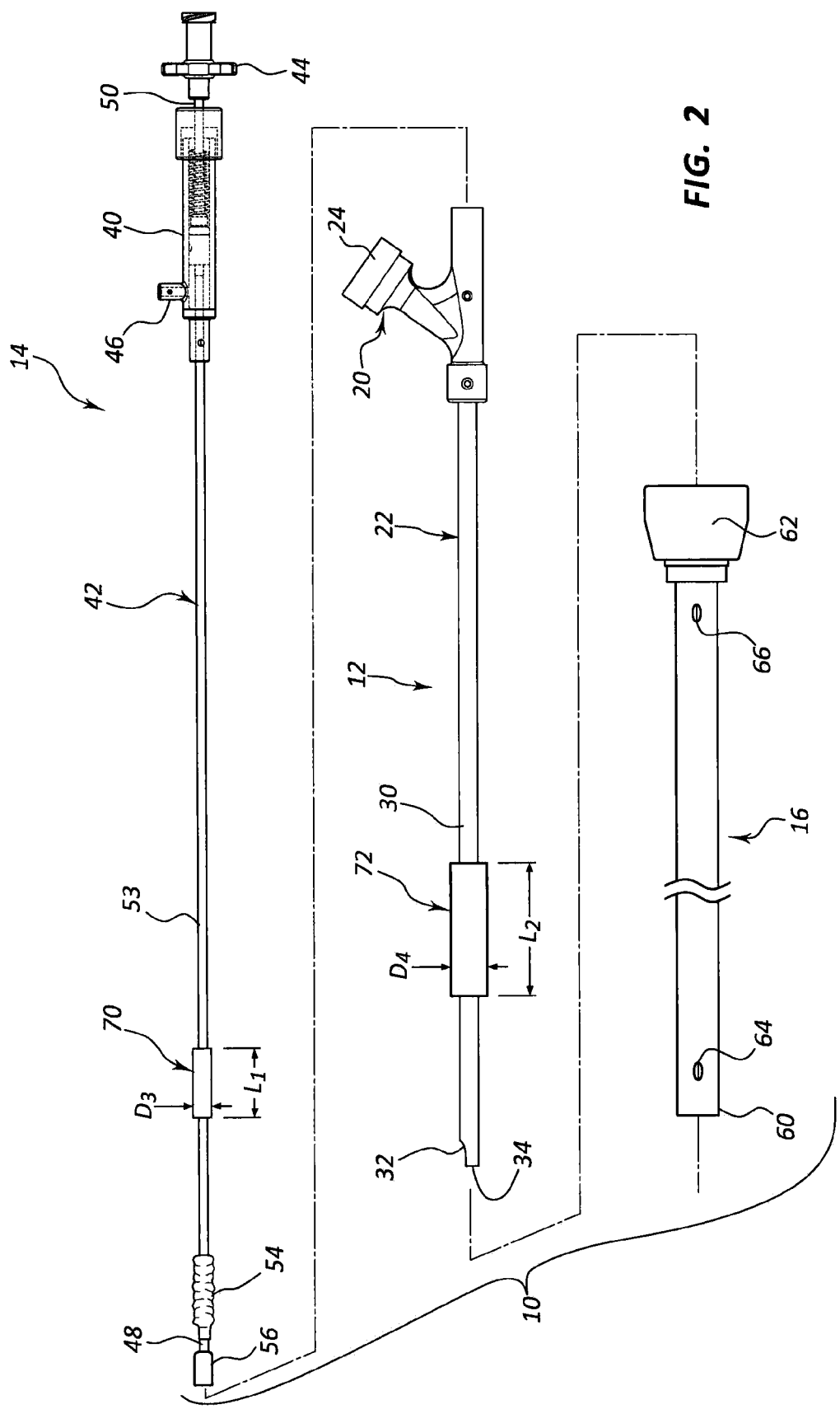
FIG. 2 is an exploded view of the vascular closure system of FIG. 1.
Figure 5:
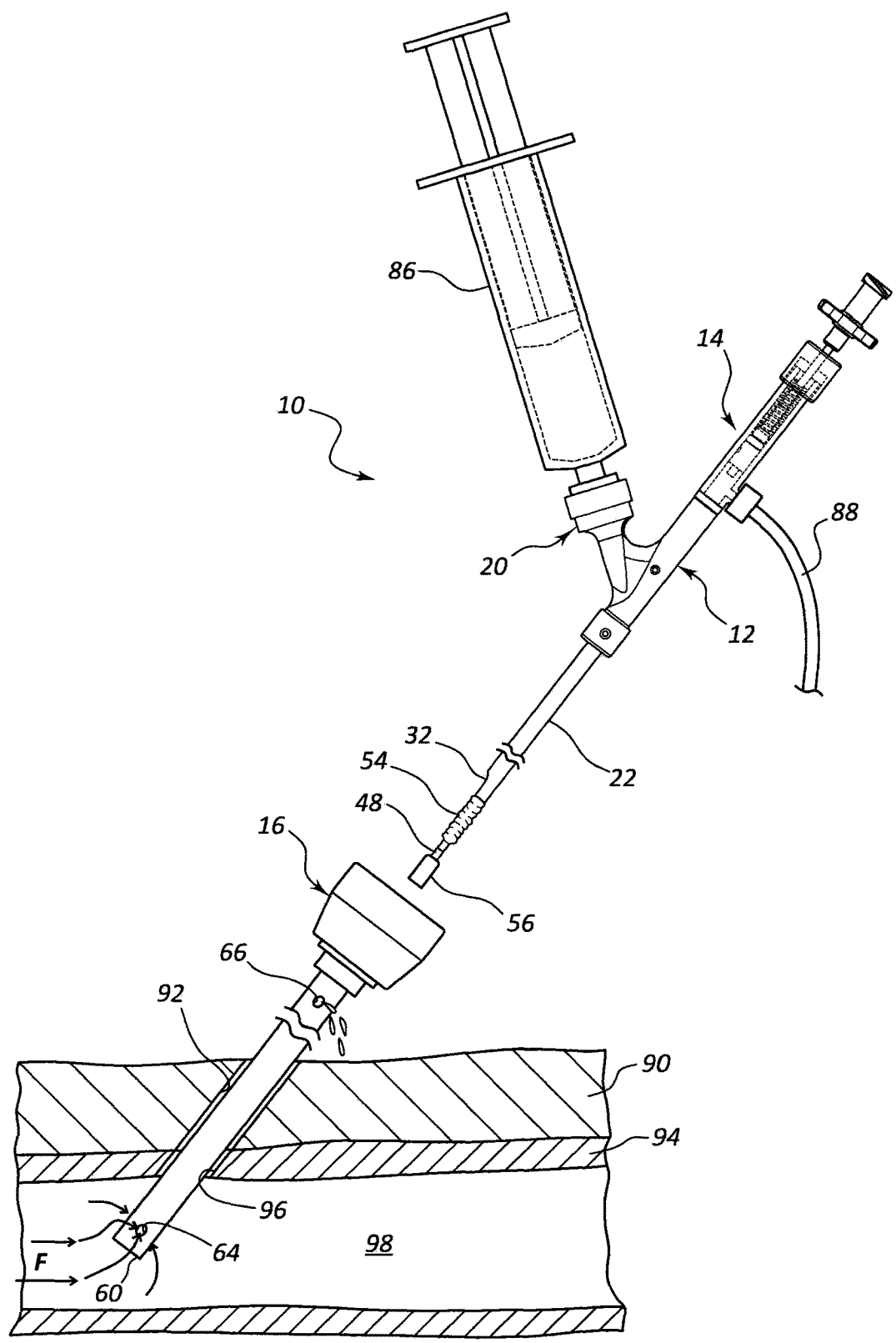
FIGS. 5-8 show the vascular closure system of FIG. 1 in use sealing a vessel puncture in accordance with the present disclosure.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "engage" and "engagable" are used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

One aspect of the present disclosure relates to a vascular closure system that includes a sealant delivery device, a balloon location device, and a sheath. Typically, a portion of the balloon location device is inserted through a lumen of the sealant delivery device. A portion of the sealant delivery device is insertable through a lumen of the sheath. The vascular closure system may include at least one sleeve mounted to at least one of the sealant delivery device, balloon location device and sheath, which helps control fluid flow in spaces defined between the devices. The at least one sleeve may help control over delivery of a bioadhesive to a vessel puncture.

In one example, the sealant delivery device includes a sealant sleeve mounted on an outer surface thereof. When the sealant delivery device with sealant sleeve is positioned within the lumen of the sheath, the sealant sleeve occupies a gap between the outer surface of the sealant delivery device and the inner surface of the sheath that defines the lumen. The sealant sleeve limits backflow of fluid into the lumen of the sheath. The liquid may be a bioadhesive sealant that is delivered by the sealant delivery device to a vessel puncture and tissue tract of a patient. The sealant sleeve limits backflow of the bioadhesive sealant into the sheath so that the bioadhesive sealant does not inhibit operation of the vascular closure system.

In another example, an inner tube sleeve is mounted to an outer surface of the balloon location device. When the balloon location device with inner sleeve are inserted into an inflation lumen of the sealant delivery device, the inner tube sleeve occupies a gap between the outer surface of the balloon location device and an inner surface of the sealant delivery device that defines the inflation lumen. The inner tube sleeve limits backflow of liquids into the inflation lumen of the sealant delivery device. For example, the inner tube sleeve may limit backflow of a bioadhesive that has been delivered by the sealant delivery device to the vessel puncture and tissue tract.

The sleeves disclosed herein may be mounted to the sealant delivery device and balloon location device using various mounting techniques such as, for example, an adhesive (e.g., a UV adhesive or glue), heat welding, laser welding, and sonic welding. The sleeves may be mounted or connected using any desired physical, chemical, thermal, or mechanical bond. The sleeves may be connected to one of the devices along an entire length of the sleeve. Other mounting techniques may be used such as, for example, mounting only one end of the sleeve such that an opposite end of the sleeve acts as a wiper seal against a surface that defines the lumen within which the device is positioned.

The sleeves may have a cross-sectional shape with maximum and minimum dimensions. The maximum dimension portion of the sleeve may contact the surface that defines the lumen within which the device is positioned, and the minimum dimension portion may provide a gap between the sleeve and the surface that defines the lumen. The maximum dimension portion of the sleeve may cover a particular feature of the device within which the sleeve is positioned such as, for example, a blood flashback port. The gap defined between the minimum dimension portion of the sleeve and the surface that defines the lumen may be used, for example, to aspirate blood from the device and the vessel puncture site. The sleeve may have a circular cross-section shape within its interior and an oval or other non-circular cross-section shape on its exterior.

The sleeves are typically positioned near the distal end of the vascular closure system near the location where the bioadhesive sealant is deposited to seal the vessel puncture and tissue tract. In some arrangements, the sleeves are positioned proximal of the distal end of the vascular closure system such as, for example, proximal of a distal outlet through which the bioadhesive sealant is ejected at the vessel puncture.

The sleeves may have a length sufficient to permit some relative axial movement between the device that carries the sleeve and the device having the lumen within which the sleeve is positioned. For example, the sheath may include a blood flashback port positioned proximal of a distal end of the sheath, and the sealant sleeve carried by the sealant delivery device has a length sufficient to maintain coverage of the blood flashback port even with some relative axial movement between the sheath and sealant delivery device.

Referring now to FIGS. 1-3B, an example vascular closure system 10 is shown and described. The vascular closure system 10 includes a sealant delivery device 12, a balloon location device 14, and a sheath 16. Typically, the balloon location device 14 is inserted through a lumen of the sealant delivery device 12. The sealant delivery device 12 is inserted through a lumen of the sheath 16. The vascular closure system 10 may include an inner tube sleeve 70 and a sealant sleeve 72. The inner tube sleeve 70 may be mounted to an outer surface of the balloon location device 14 and positionable within a lumen of the sealant delivery device 12. The sealant sleeve 72 may be mounted to an outer surface of the sealant delivery device 12 and positionable within the sheath 16. The inner tube sleeve 70 and sealant sleeve 72 may be positioned and operable to limit backflow of bioadhesive sealant delivered by the sealant delivery device 12 to seal a vessel puncture.

The sealant delivery device 12 includes a manifold 20 and a dual lumen tube 22. The manifold 20 includes an injection port 24 used to connect the sealant delivery device 12 to a source of sealant. The dual lumen tube 22 includes first and second lumens 26, 28 and has an outer surface 30. The first lumen 26 includes a distal open end 32. The second lumen 28 includes a distal open end 34. The second lumen 28 includes a lumen diameter $D_1$.

The balloon location device 14 includes a housing 40, an inner tube 42, an inner tube manifold 44, and an inflation port 46. The inner tube 42 has distal and proximal ends 48, 50 and an outer surface 53, and defines an inner tube lumen 52. A balloon 54 may be positioned at the distal end 48. A detachable tip 56 may be positioned distal of the balloon 54. The proximal end 50 of the inner tube 42 may extend proximal of the housing 40. The inner tube manifold 44 may be mounted to the proximal end 50. The inner tube 42 may move axially relative to the housing 40. This axial movement within the housing 40 may be visible by an operator and may provide some indication of a condition of the balloon 54 (e.g., a fill condition, an inflation pressure, or relative position between balloon 54 and a distal end of the dual lumen tube 22).

Sheath 16 may include a distal end 60, a hub 62, a blood inlet 64, a blood outlet 66, and a sheath lumen 68. The blood inlet 64 and blood outlet 66 may be referred to as blood flashback ports. In some arrangements, sheath 16 may include a plurality of blood inlets 64 and a plurality of blood outlets 66. A blood inlet may be connected in fluid communication with a particular one of the blood outlets. Typically, the blood inlet 64 receives a flow of blood therein when the distal end 60 is positioned within or exposed to blood such as blood flow within a vessel. Blood flows out of the blood outlet 66 to show the operator when the blood inlet 64 is positioned in or removed from the blood flow within the vessel. The sheath lumen 68 may define a sheath inner diameter $D_2$ (see FIG. 1B).

The inner tube sleeve 70 has a length $L_1$ and an inner tube sleeve outer diameter $D_3$. Sealant sleeve 72 has a length $L_2$ and a sealant sleeve maximum outer diameter $D_4$. An alterative sealant sleeve 172 shown in FIG. 1C has a non-circular outer profile that includes the maximum outer diameter $D_4$ and also a sealant sleeve minimum outer diameter $D_5$. A difference between the sealant sleeve minimum outer diameter $D_5$ and the sheath inner diameter $D_2$ defines an aspiration gap 174. The aspiration gap 174 may be used to aspirate or remove materials within sheath 16. The materials may include, for example, blood that has collected in sheath 16 via blood flow through the blood inlet 64 and blood outlet 66.

Referring to FIG. 1A, the inner tube sleeve 70 may occupy a gap between the outer surface 53 of the inner tube 42 and the surface defining the second lumen 28. In one example, the inner tube sleeve 70 is mounted directly to the outer surface 53 along the entire length $L_1$. A small gap may be defined between the outer surface of the inner tube sleeve 70 and the surface defining the second lumen 28. In one example, the gap is in the range of about 0.0005 inches and 0.005 inches, and more preferable in the range of about 0.0005 inches and 0.002 inches or less.

The inner tube sleeve 70 may have a thickness in the range of about 0.001 inches to about 0.004 inches. The length $L_1$ of inner tube sleeve 70 may be in the range of about 2 mm to about 20 mm, and more preferably in the range of about 3 mm to about 10 mm in length.

Sealant sleeve 72 may be mounted directly to the outer surface 30 of the dual lumen tube 22. The sealant sleeve 72 may be connected along its entire length $L_2$ to the outer surface 30. A small gap may exist between an outer surface of the sealant sleeve 72 and the surface defining the sheath lumen 68. The gap may be in the range of about 0.0005 inches to about 0.005 inches, more preferably in the range of about 0.0005 inches to about 0.002 inches or less.

Sealant sleeve 72 may have a thickness $T_2$ in the range of about 0.001 inches to about 0.01 inches. The length $L_2$ of sealant sleeve 72 is preferably in the range of about 0.5 cm to about 1.5 cm, and more preferably in the range of about 0.9 cm to about 1.1 cm.

The inner tube sleeve 70 and sealant sleeve 72 may comprise a polymer material including polyamides, polyolefins, fluoropolymers, polyurethanes, polyureas, hydrogenated polyacrylonitriles, polyacrylates and polymethacrylates, to name a few. Specific examples include Nylon, Pebax™, Pellethane™, PTFE, and FEP. The inner tube sleeve 70 and sealant sleeve 72 may further comprise a cured elastomer such as a silicone elastomer or fluorinated elastomer such as FKM. The inner tube sleeve 70 and sealant sleeve 72 may further comprise a lubricating agent on the surface such as a silicone oil.

In at least some arrangements, the sealant delivery device 12 is moved axially relative to the sheath 16 once the sheath 16 is positioned within a tissue tract leading to the vessel puncture. For example, once the sheath 16 is positioned within the tissue tract, the balloon 54 is inflated and the balloon location device 14 and sealant delivery device 12 are withdrawn together proximally until the inflated balloon 54 contacts an inner surface of the vessel adjacent to the vessel puncture. The sealant delivery device 12 operates to deposit a volume of sealant outside of the vessel to seal the vessel puncture. In a later step, the balloon 54 is deflated and withdrawn through the vessel puncture and the detachable tip 56 is deposited within the volume of sealant that has been deposited by the sealant delivery device 12. The sealant sleeve 72 may have a length $L_2$ sufficient to provide the desired blockage of the bioadhesive sealant backflow into sheath lumen 68 (e.g., through blood inlet 64 or opening at distal end 60) through a range of relative axial positions between the sealant delivery device 12 and sheath 16.

Referring to FIG. 3B, an alternative attachment for sealant sleeve 72 to sealant delivery device 12 is shown. The sealant sleeve 72 may be attached to the outer surface 30 of the dual lumen tube 22 at a proximal end 73 of the sealing sleeve 72. An opposite distal end 75 is detached from the outer surface 30. The distal end 75 may be flared radially outward from dual lumen tube 22 to help maintain contact with the surface defining the sheath lumen 68. The distal end 75 may provide a seal with the surface defining the sheath lumen 68 and may be referred to as a wiper seal.

Referring to FIG. 4A, another example sleeve attachment is shown. The inner tube sleeve 70 is attached to an outer surface of the inner tube 42, which may include first and second tube portions 80, 82. The second tube portion 82 may be inserted into the first tube portion 80. The inner tube sleeve 70 may overlap a junction between the first and second tube portions 80, 82. Inner tube sleeve 70 may be connected to both of the first and second tube portions 80, 82. In one example, an adhesive is used to connect the inner tube sleeve 70 to both of the first and second tube portions 80, 82. The inner tube sleeve 70 may be used to connect together the first and second tube portions 80, 82.

Referring to FIG. 4B, in other embodiments, alterative bonding arrangements may be used to connect the inner tube sleeve 70 to the inner tube 42. For example, laser bonding may be used to create bond areas 84A-C between the inner tube 42 and inner tube sleeve 70. The bond areas 84A-C may include reflow of a polymer material of the inner tube sleeve 70 and polymer materials of the first and second tube portions 80, 82.

Referring now to FIGS. 5-8, an example method is described for sealing a vessel puncture 96 using the vascular closure system 10. In a first step shown in FIG. 5, the sheath 16 is inserted through a tissue tract 92 formed in a tissue layer 90 and through vessel puncture 96 and vessel 94 to gain access to blood flow F within the vessel interior 98. The blood inlet 64 is exposed to the blood flow F. Blood flows through the sheath 16 to the blood outlet 66 to provide a visual indicator to the operator that the distal end 60 is within the vessel interior 98. The sealant delivery device 12 and balloon location device 14 may be advanced through the sheath 16 prior to or after the sheath 16 has been positioned within the vessel interior 98. Blood may remain in the sheath 16 during further operational steps for the vascular closure system 10.

Figure 6:
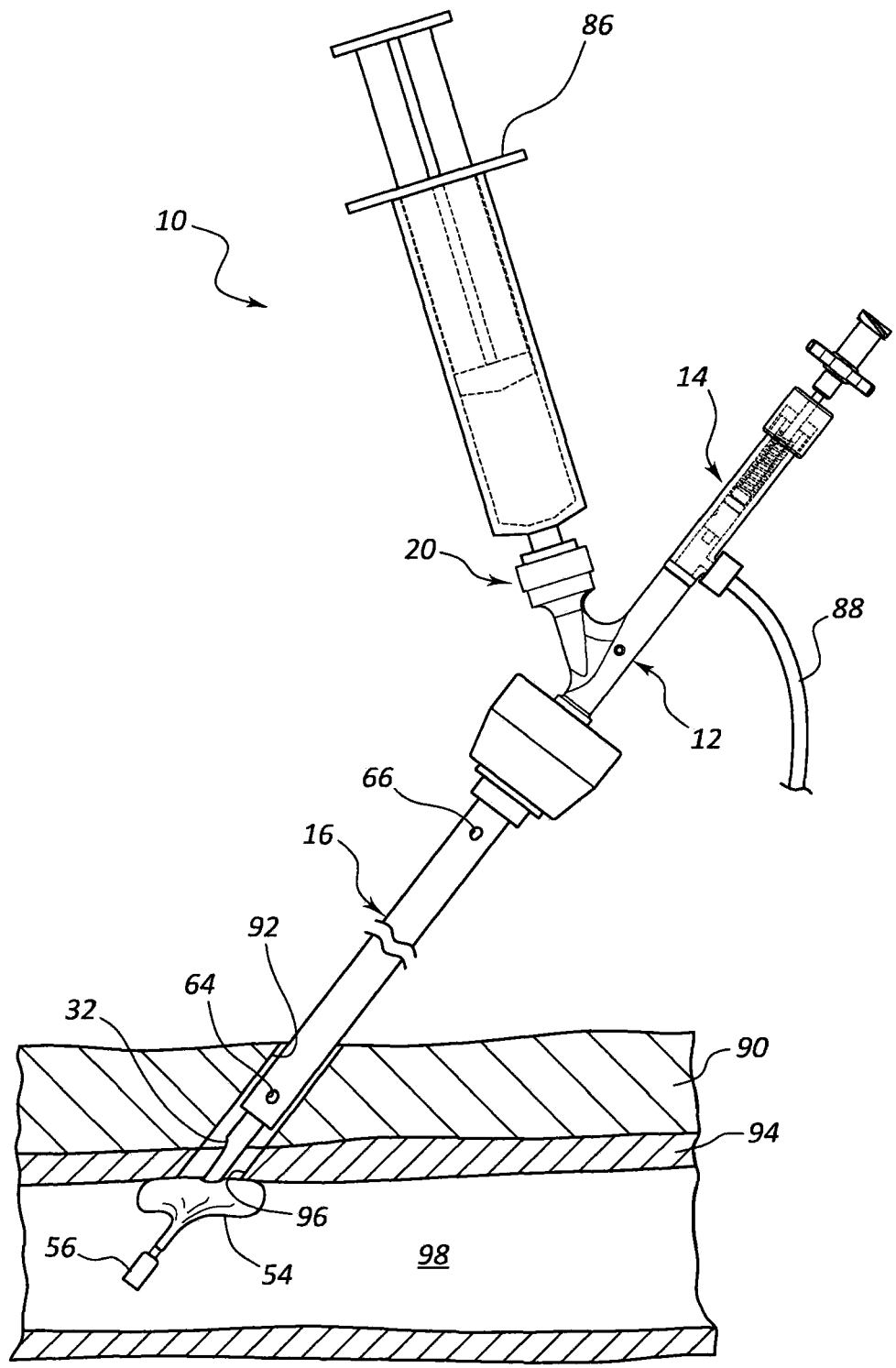

Referring now to FIG. 6, the operator advances the sealant delivery device 12 and balloon location device 14 to position the balloon 54 within the vessel interior 98. In some arrangements, the sealant delivery device 12 and balloon location device 14 may be connected together and move together relative to sheath 16. The balloon 54 is inflated within vessel 94 via an inflation source 88 connected in fluid communication with balloon location device 14. Balloon 54 is withdrawn proximally to contact balloon 54 against an inner surface of the vessel 94 adjacent to the vessel puncture 96 to temporarily seal the vessel puncture 96 from within the vessel 94. The distal end 60 of sheath 16 is positioned within tissue tract 92 at a location proximal of the vessel puncture 96 and typically proximal of distal open ends 32, 34 of the first and second lumens 26, 28 of dual lumen tube 22.

Figure 7:
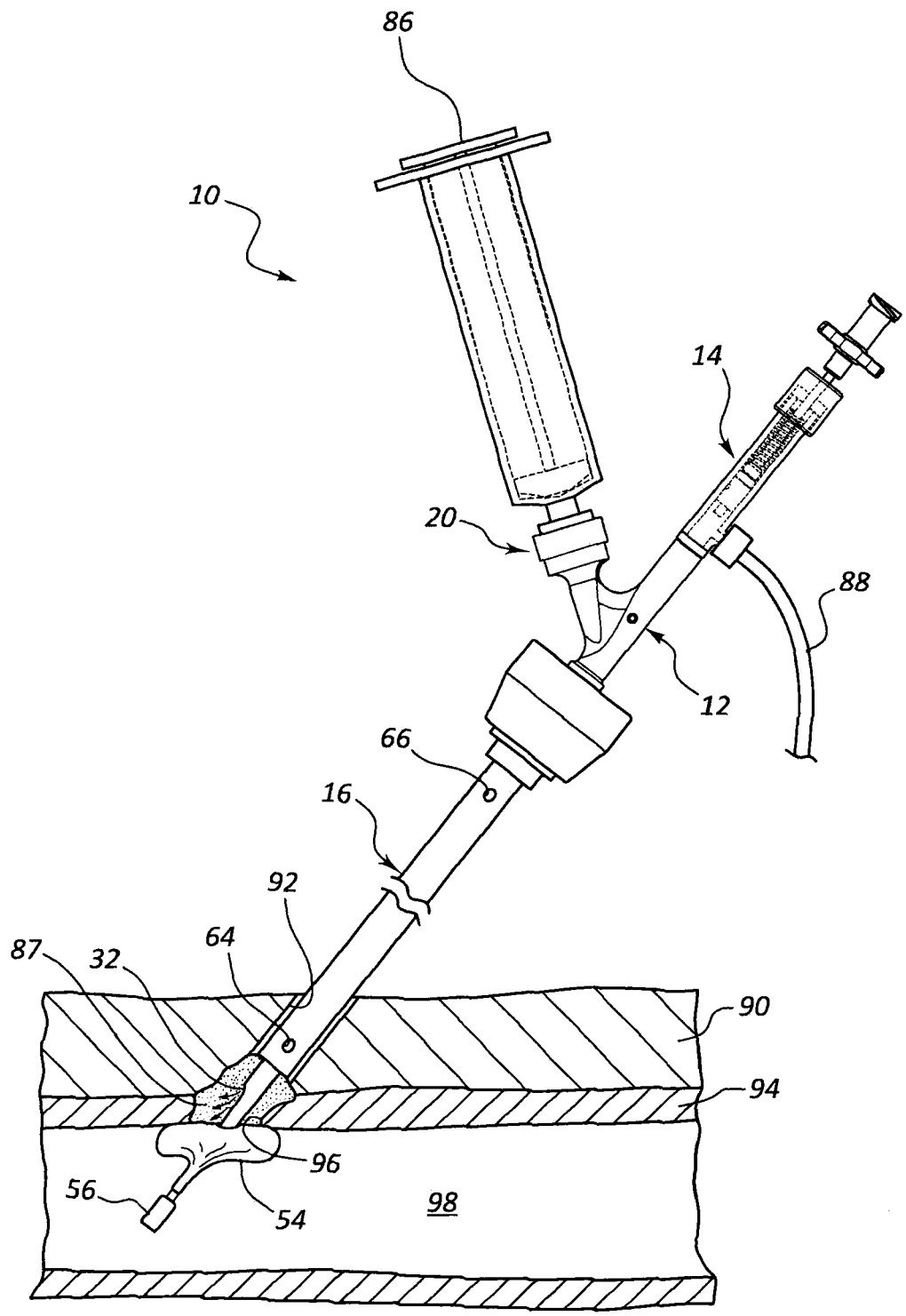

Referring now to FIG. 7, a sealant source 86 is connected to the injection port 24 of the manifold 20 of sealant delivery device 12. The sealant source 86 advances a volume of sealant through the first lumen 26 of dual lumen tube 22 and into tissue tract 92 and vessel puncture 96. As the volume of sealant flows into the tissue tract 92 and vessel puncture 96 in and around the distal end 60 of sheath 16 and distal open end 34 of the second lumen 28, the inner tube sleeve 70 and sealant sleeve 72 limit backflow of the sealant into the second lumen 28 and sheath lumen 68, respectively. The sealant sleeve 72 may cover blood inlet 64 to limit flow of sealant through blood inlet 64 into the sheath lumen 68. Sealant sleeve 72 may also limit flow of sealant into the sheath lumen 68 via an opening at the distal end 60 of sheath 16.

Figure 8:
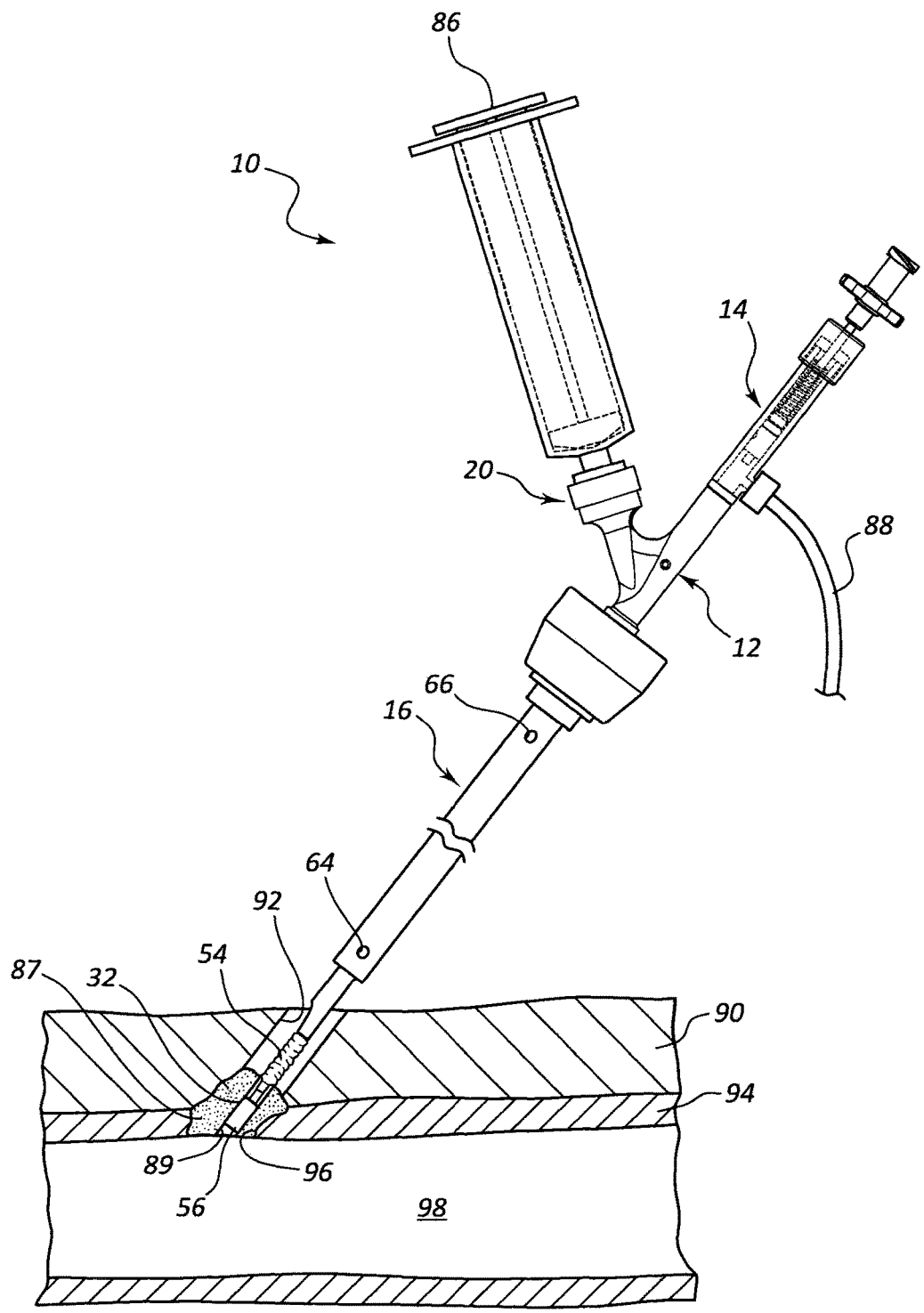

Referring to FIG. 8, the sealant cures to form a sealant plug 87. A sealant channel 89 may be formed in sealant plug 87 when removing the dual lumen tube 22 and balloon 54 proximally through sealant plug 87. The sealant delivery device 12 and balloon location device 14 are withdrawn until the detachable tip 56 is positioned within the sealant channel 89. The balloon location device 14 is operated to detach the detachable tip 56 within the sealant plug 87 to provide further sealing of vessel puncture 96 and tissue tract 92.

In some arrangements, a secondary sealant is ejected through one of the inner tube 42 and sealant delivery device 12. The secondary sealant may fill sealant channel 89. The secondary sealant may form a second layer of sealant proximal of the sealant plug 87. The secondary sealant may be used in place of the detachable tip 56. Alternatively, the secondary sealant may be used in addition to the detachable tip 56. The balloon location device 14 may be withdrawn further proximally beyond the position shown in FIG. 8 for purposes of depositing the secondary sealant proximal of the sealant plug 87. The inner tube sleeve 70 may assist in limiting backflow of the secondary sealant into second lumen 28 during depositing of the secondary sealant in the tissue tract 92.

The vascular closure system 10 may be operable with one or both of inner tube sleeve 70 and sealant sleeve 72. The vascular closure system 10 may include a plurality of inner tube sleeves 70 positioned between sealant delivery device 12 and balloon location device 14 and a plurality of sealant sleeves 72 positioned between sealant delivery device 12 and sheath 16. When a plurality of one of the sleeves 70 or 72 is included, the sleeves 70, 72 may be positioned in series (e.g., end-to-end) or at least partially overlapping each other (e.g., stacked one on top of another).

The inner tube sleeve 70 and sealant sleeve 72 may be referred to as fluid blocking members that block fluid flow through at least a portion of the vascular closure system 10. The inner tube sleeve 70 and sealant sleeve 72 may be referred to as bearing members that provide a bearing surface between members (i.e., sealant delivery device 12, balloon location device 14, and sheath 16) of the vascular closure system 10. The inner tube sleeve 70 and sealant sleeve 72 may include materials that provide at least some lubricity to decrease friction between members of the vascular closure system 10 to improve ease in assembling and providing relative axial movement therebetween during use. The inner tube sleeve 70 and sealant sleeve 72 may be referred to as interface members that provide a physical interface between members of the vascular closure system 10.

The sealants discussed herein may comprise a single component, or may comprise multiple sealant components that are mixed together. The multiple sealant components may further react together to form a cross-linked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include proteinaceous compositions such as albumin, collagen and polylysine. Other examples include carbohydrate compositions such polyhyaluronic acid. The sealant components may also contain reactive functional groups to promote chemical cross-linking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A closure assembly, comprising:
   an insertion sheath insertable into a tissue puncture, the insertion sheath having a sidewall and a distal end;
   at least one location port defined in the sidewall at the distal end of the insertion sheath;
   a tissue puncture closure device insertable through the insertion sheath and into the tissue puncture, the tissue puncture closure device comprising:
   a dual lumen delivery tube having a first lumen configured to deliver a volume of sealing material to the tissue puncture, and a second lumen sized for insertion of a balloon location device;
   a first sealing sleeve, the first sealing sleeve being positioned between an outer surface of the dual lumen delivery tube and an inner surface of the insertion sheath to limit backflow of the sealing material into the insertion sheath, the first sealing sleeve blocking the at least one location port at the distal end of the insertion sheath, the first sealing sleeve contacting the inner surface of the insertion sheath at a plurality of spaced apart locations around a circumference of the inner surface, wherein there is no contact between the first sealing sleeve and the inner surface of the insertion sheath between each of the plurality of spaced apart locations;
   a second sealing sleeve, the second sealing sleeve being connected to an outer surface of the balloon location device and positioned between the outer surface of the balloon location device and an inner surface of the second lumen to limit back flow of the sealing material into the second lumen, the second sealing sleeve being configured to seal the inner surface of the second lumen of the delivery tube during depositing of the sealing material via the first lumen.

2. The closure assembly of claim 1, wherein the first sealing sleeve is connected to the outer surface of the dual lumen delivery tube.

3. The closure assembly of claim 1, wherein the second sealing sleeve is connected to the outer surface of the balloon location device.

4. The closure assembly of claim 1, wherein the first and second sealing sleeves comprise a continuous loop of compliant material.

5. The closure assembly of claim 1, wherein the first and second sealing sleeves have a tubular construction with a circular cross section.

6. The closure assembly of claim 1, wherein the first sealing sleeve has an oval shaped outer perimeter and a circular shaped inner perimeter.

7. The closure assembly of claim 1, wherein the first sealing sleeve is connected to the dual lumen delivery tube with an adhesive.

8. The closure assembly of claim 1, wherein the first sealing sleeve is connected to the dual lumen delivery tube with a heat weld.

9. The closure assembly of claim 1, further comprising an inflation balloon positioned at a distal end of the balloon location device, the second sealing sleeve being positioned proximal of the inflation balloon.

10. The closure assembly of claim 1, wherein the first sealing sleeve is connected to the inner surface of the insertion sheath.

11. A tissue puncture closure device, comprising:
    a balloon location device having an inflation balloon positioned at a distal end portion thereof;
    an insertion sheath having a distal end and at least one location port positioned laterally through the distal end;
    a delivery tube having a first lumen configured to deliver a volume of sealant and a second lumen sized to receive the balloon location device, a distal end of the delivery tube being insertable through the insertion sheath to a tissue puncture;
    a first sealing sleeve positioned between an outer surface of the delivery tube and an inner surface of the insertion sheath to limit backflow of the volume of sealant into the insertion sheath, the first sealing sleeve covering the at least one location port at the distal end of the insertion sheath, the first sealing sleeve contacting the inner surface of the insertion sheath at a plurality of spaced apart locations around a circumference of the inner surface, wherein there is an absence of contact between the first sealing sleeve and the inner surface of the insertion sheath between each of the plurality of spaced apart locations;
    a second sealing sleeve connected to an outer surface of the balloon location device and positioned between the outer surface of the balloon location device and an inner surface of the second lumen, the second sealing sleeve being configured to limit backflow of the volume of sealant into the second lumen during depositing of the volume of sealant via the first lumen.

12. The tissue puncture closure device of claim 11, wherein the first and second sealing sleeves are continuous tubular-shaped structures.

13. The tissue puncture closure device of claim 11, wherein the first and second sealing sleeves comprise compliant material.

14. The tissue puncture closure device of claim 11, wherein at least one of the first and second sealing sleeves has a circular inner cross-sectional shape and a non-circular outer cross-sectional shape.

15. The tissue puncture closure device of claim 11, wherein the first sealing sleeve is connected to the delivery tube and the second sealing sleeve is connected to the balloon location device.

* * * * *